United States Patent [19]
Park

[11] Patent Number: 5,823,982
[45] Date of Patent: Oct. 20, 1998

[54] TRACTION APPARATUS FOR PHYSICAL THERAPY OF HERNIATED NUCLEOSUS PULPOSUS OR SPRAIN AND STRAIN

[76] Inventor: Chang Joon Park, 244-326, Sangdo-4-dong, Dongiak-ku, Seoul, Rep. of Korea

[21] Appl. No.: 785,042

[22] Filed: Jan. 17, 1997

[30] Foreign Application Priority Data

Jan. 18, 1996 [KR] Rep. of Korea ...................... 1996 970

[51] Int. Cl.⁶ ....................................................... A61F 5/00
[52] U.S. Cl. ............................................... 602/36; 602/32
[58] Field of Search ................................ 602/18, 32, 36, 602/38–40; 128/DIG. 20, 23; 601/33, 39; 606/241, 242

[56] References Cited

U.S. PATENT DOCUMENTS

| | | | |
|---|---|---|---|
| 1,648,970 | 11/1927 | Strelow | 128/DIG. 20 X |
| 3,892,229 | 7/1975 | Taylor. | |
| 3,942,518 | 3/1976 | Tenteris. | |
| 4,099,523 | 7/1978 | Lowrey. | |
| 4,178,922 | 12/1979 | Curlee | 128/DIG. 20 X |
| 4,543,947 | 10/1985 | Blackstone. | |
| 4,715,362 | 12/1987 | Scott. | |
| 4,745,922 | 5/1988 | Taylor. | |
| 5,382,226 | 1/1995 | Graham. | |
| 5,441,479 | 8/1995 | Chitwood | 602/18 |

FOREIGN PATENT DOCUMENTS

| | | |
|---|---|---|
| 21 29 140 A | 12/1972 | Germany. |
| 33 18 938 A | 11/1984 | Germany. |
| 90 00 599 U | 9/1990 | Germany. |
| WO 95 07669 A | 3/1995 | WIPO. |
| WO 95/07669 A1 | 3/1995 | WIPO. |

*Primary Examiner*—Richard J. Apley
*Assistant Examiner*—Denise Pothier
*Attorney, Agent, or Firm*—Staas & Halsey

[57] ABSTRACT

Traction apparatus for medically and physically treating herniated nucleosus pulposus or sprain and strain is disclosed. The traction apparatus comprises an upper support frame, a lower support frame, and a plurality of tubes. The traction apparatus further includes an exercising device. The upper support frame encircles the upper part of the therapy region and has two free ends positioned in space relation. The lower support frame encircles the lower part of the therapy region and hits two free ends positioned in space relation. The tubes are expandable to provide traction on the therapy region and are filled up with fluid which is generated by a fluid generating device. Preferably, the fluid generating device is a programmed controller including additionally pressure regulating function, timing function, intermittent ON and OFF function, etc.

7 Claims, 5 Drawing Sheets

TRACTION APPARATUS FOR PHYSICAL THERAPY OF HERNIATED NUCLEOSUS PULPOSUS OR SPRAIN AND STRAIN

FIELD OF THE INVENTION

The present invention relates to a medical aid appliance, and more particularly to a traction apparatus for physical therapy of herniated nucleosus pulposus or sprain and strain.

BACKGROUND OF THE INVENTION

The herniated nucleosus pulposus (hereinafter referred to as "HNP"), which is limited to the explanations thereof with omitting the explanations of the sprain and strain, is one of vertebral diseases. The HNP is caused by the herniation of the nucleosus pulposus of disk which is interposed between one vertebra and one adjacent vertebra. Excessive loads and external impacts trigger a person to the HNP. The HNP takes place at cervical region, thoracic region, or lumbar region of a vertebral column. The HNP sufferers undergo lumbago most of all because the nerves root and is pressed also undergo radiating pain as the lower half of sufferers' body. If the sufferers take a turn for the worse, they cannot perform their normal activities and, moreover cannot lead a normal daily life.

Accordingly, as number of attempts have been made to treat the NHP. Various therapy techniques, for example, operating therapy technique, physical therapy technique including bed rest therapy, therapy by hot heat, optical therapy, electrotherapy, traction therapy, and mediation technique, may have been used for the treatment of the HNP.

The traction therapy is one physical therapy of providing traction forces at the therapy region or eliminating or minimizing compressive forces on the vertebral disks or on bone structure in the cervical, lumbar, sacral, or pelvic region to alleviate tension and pressure applied to the disks and the bone structure. The traction apparatus are mainly divided into two types. One type is a traction apparatus for cervical region and the other type is a traction apparatus for lumbar region.

First, well known traction apparatus for treating the cervical HNP apply traction forces to neck of the patient just as the neck is in a fixed condition. Therefore, the traction apparatus for the cervical region have the problems that they require the patient to be confined to chair or other complicated and/or restrictive device that does not allow the patient sufficient freedom to perform productive functions or other normal activities. There is also the problem that it is difficult to increase or decrease the traction forces in accordance with the symptoms of the patient and to minutely and accurately change the traction forces.

Next, well known traction apparatus for treating the lumbar HNP are similar to the cervical traction apparatus. Thus, the lumbar traction apparatus have the disadvantages that they require the patient to be hospitalized or at least confined to bed. Consequently, the recovery period is tedious and the patient is often tempted to prematurely return to normal activities before recovery is complete.

Considering the prior art of an ambulatory lumbo-sacral traction system, the traction system is disclosed in U.S. Pat. No. 4,715,362. The traction system comprises an upper support member 16, a lower support member 12, and a plurality of compressible struts 13 which are positioned between the upper support member 16 and the lower support member 12 and receive respective spring 34 therein to permit a patient to be ambulatory while undergoing traction system.

According to the ambulatory traction system, tho patient is able to walk around with his arms free and is able to sit and stand at will. However, to adjust the length of the struts 13, namely, the magnitude of traction forces being applied to the patient, which may be accomplished by rotating the inner tube 32 with respect to the outer tube 33 to migrate longitudinally the projection 36 along the coil spring 34. Consequently, the prior art according to the ambulatory traction system has the severe disadvantages and problems that the struts must be individually adjusted in longitudinal force and it is difficult to minutely and precisely change the traction forces. Also, there is the drawback that the patient is ambulatory but does not exercise naturally and freely the therapy region.

In view of the limitations and drawbacks of the afore-described treatment, there is a need for a traction apparatus which permits a patient not only to be ambulatory while providing precisely and simply adjustable traction but to exercise the therapy region with ease.

SUMMARY OF THE INVENTION

It is an object of the present invention to provide a new and improved traction apparatus for physically treating herniated nucleosus pulposus or sprain and strain wherein a patient undergoing the treatment can exercise naturally and freely in the therapy region by rotation, flexion, and extension actions.

It is another object of the present invention to provide a new and improved traction apparatus for physically treating herniated nucleosus pulposus or sprain and strain wherein the magnitude of the traction forces can be precisely and minutely adjusted in accordance with the symptoms of the patient.

It is further object of the present invention to provide a new and improved traction apparatus for physically treating herniated nucleosus pulposus or sprain and strain wherein the traction apparatus can additionally perform pressure regulating function, timing function, intermittent ON and OFF function, displaying function, etc.

According to the present invention, these objects and advantages are achieved. There is provided a traction apparatus comprising an upper support frame for supportably encircling upper part of a patient's therapy region and having two free ends positioned in space relation therebetween, with a first adjustable fastening device to connect the two free ends; a lower support frame for supportably encircling lower part of the patient's therapy region and having two free ends positioned in space relation therebetween, with a second fastening device to connect the two free ends; a traction device operatively positioned between the upper support frame and the lower support frame for encircling the therapy region and for providing the therapy region with variable traction forces, and the traction device having a plurality of expandable tubes wherein each of the tubes forms at least one closed compartment itself in flow communication with adjacent tubes and has two free ends positioned in space relation therebetween; a device sealably connected to the traction device for supplying the traction device with fluid pressures corresponding to the traction forces.

The various features of novelty which characterize the invention are pointed out with particularity in the claims annexed to and forming a part of this disclosure.

For a better understanding of the invention, its operating advantages and specific objects attained by its uses, reference is made to the accompanying drawings and descriptive matter in which the preferred embodiments of the invention are illustrated.

DETAILED DESCRIPTIONS OF THE PREFERRED EMBODIMENTS

This invention will be described in further detail by way of embodiments with reference to to accompanying drawings.

Figure 1:
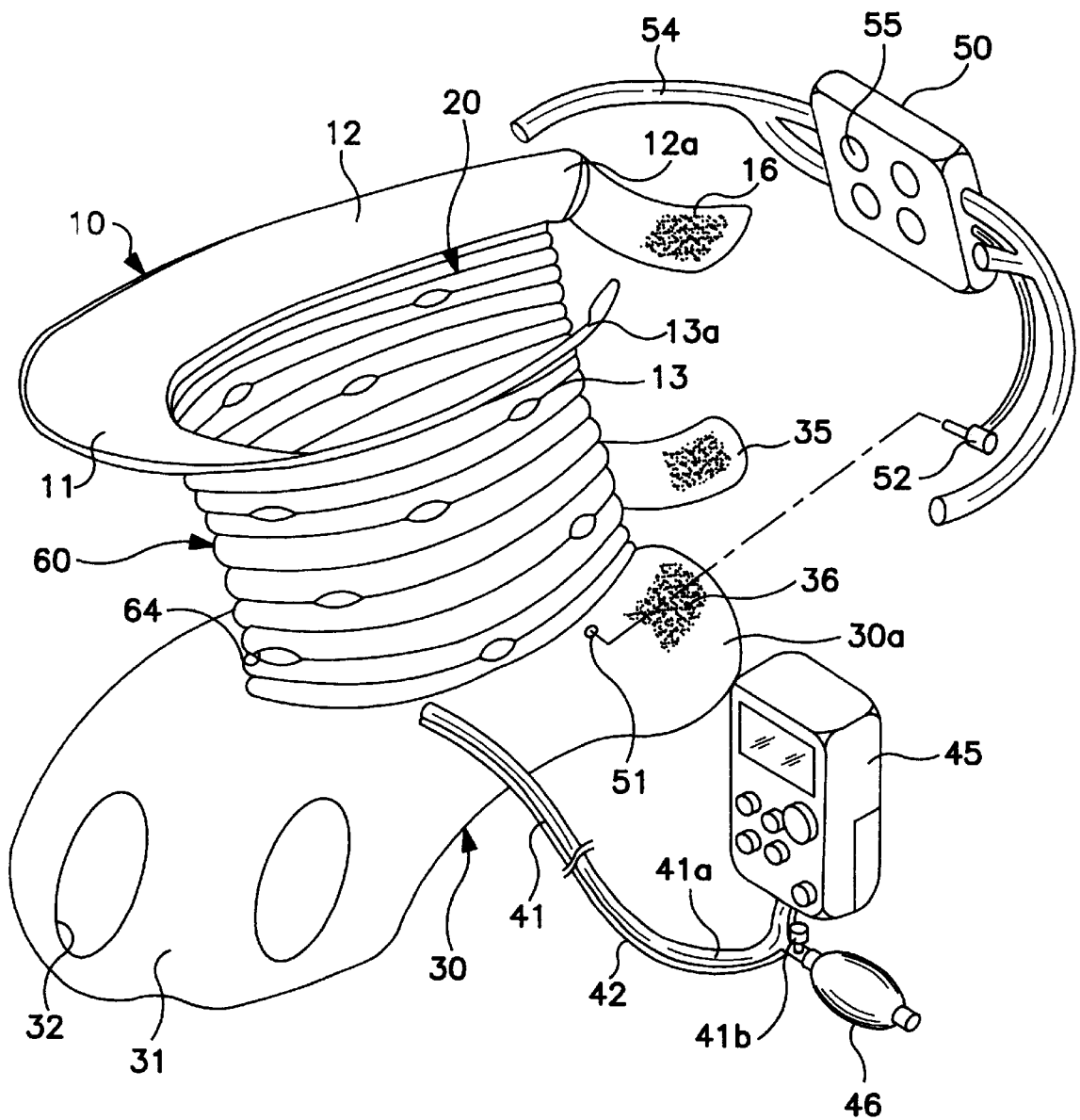
FIG. 1 is a perspective view of a traction apparatus according to the present invention which is used at the cervical region and shows the state of applying sufficient traction force.

Referring to FIG. 1, there is shown an embodiment of a traction apparatus for treating the cervical HNP according to the present invention. The traction apparatus for the cervical HNP includes an upper support frame 10 which encircles the upper part of the cervical region extending from the bottom of jaw to the back portion of neck to support the upper part of the cervical region. Front portion 11 of the upper support frame 10 has a shape adapted to support the bottom of the jaw. Left portion 12 and right portion 13 extending from the front portion 11 has a shape adapted to encircle and support the side portions and the back portion of the neck. The left and right portions 12 and 13 have each free end which is spaced apart therebetween to wear the traction apparatus through the head of the patient. End portions 12a and 13a of the left and right portions 12 and 13 have complementary velcro fastener 16 which adhere when pressed together.

A exercising device 20 is rotatably fixed at the bottom of the upper support frame 10. Examining the exercising device 20 with respect to FIG. 4A, FIG. 4B and FIG. 5, the exercising device 20 has an upper member 22 and a lower member 24. The upper member 22 has a elongated protrusion 22a formed along a center line of bottom surface thereof, and the lower member 24 has a elongated groove 24a formed along a center line of top surface thereof so that the protrusion 22a of the upper member 22 is slidably fitted with the groove 24a of the lower member 24. Preferably, the lubricant is instilled into the inside of the exercising device 20, and the upper and lower members 22 and 24 are made of magnetic material with same polarity to generate repulsive force therebetween and also are made of rubber to make the weight of the members 22 and 24 lighter than other magnetic material with a larger specific gravity. Thus, the upper member 22 rotates smoothly and slidably with respect to the fixed lower member 24. On the other hand, the exercising device 20 may be additionally provided on the traction apparatus and is excluded from the traction apparatus when the therapy region must be absolutely fixed.

Again referring to FIG. 1, a lower support from 30 is provided at the lower side of the traction apparatus according to the present invention. The lower support frame 30 has two free ends of end portions 30a which are spiced apart therebetween as the upper support frame 10. The end portions 30a have VELCRO fasteners 35 and 36 as the end portions 12a and 13a of the upper support frame 10. Two ventilation openings 32 are formed at front portion 31 of the lower support frame 30.

A flexible pipe 41 is inserted into the lower support frame 30 to supply fluid, for example, air. The pipe 41 is bifurcated with one end portion 41a and the other end portion 41b. An automatic fluid generation device 45 is detachably connected to the end portion 41a of the pipe 41 and a manual fluid generating device 46, for example, a pressure bulb, is also detachably connected to the other end portion 41b of the pipe 41 to to enable the patient to be more active 45 and 46 after wearing the traction apparatus. The manual fluid generating device 46 prepares against troubles of the automatic fluid generating device 45. On the other hand, the devices 45 and 46 may be selected among well know prior arts for automatically or manually generating fluid. Therefore, the detailed descriptions of the devices 45 and 46 are omitted in here.

Preferably, the automatic fluid generating device 45 may additionally perform pressure regulating function, timing function, intermittent ON and OFF functions, displaying function, etc., what is more. The automatic device 45 may be a programmed controller including the above function. Since the device 45 may be easily manufactured by an ordinally skilled person, the explanation of associated constitutions is omitted in here. Also, preferably, the traction apparatus according the present invention includes a small-sized and detachable electrotherapy device 50 to relax tonus of muscle and ligament before the traction therapy.

To operatively include the electrotherapy device 50, an electric wire 12 to attached to the pipe 41. The automatic device 46 has a power source, for example, a battery, or an adapting device for supplying a power source of alternating current. The wire 42 extends to a socket 51 which is mounted in or on a predetermined position of the lower support frame 30. A jack 52 of the electrotherapy device 50 is fitted with the socket 51. And, the electrotherapy device 50 has bands 54 for enclosing the neck to closely adhere the electrotherapy device 50 against the therapy region. Numeral 55 designates electrode terminals for generating hot heat. Of course, the electrotherapy device 50 may be applied to the therapy region independently of the traction apparatus according to the present invention before the traction treatment.

Figure 3:
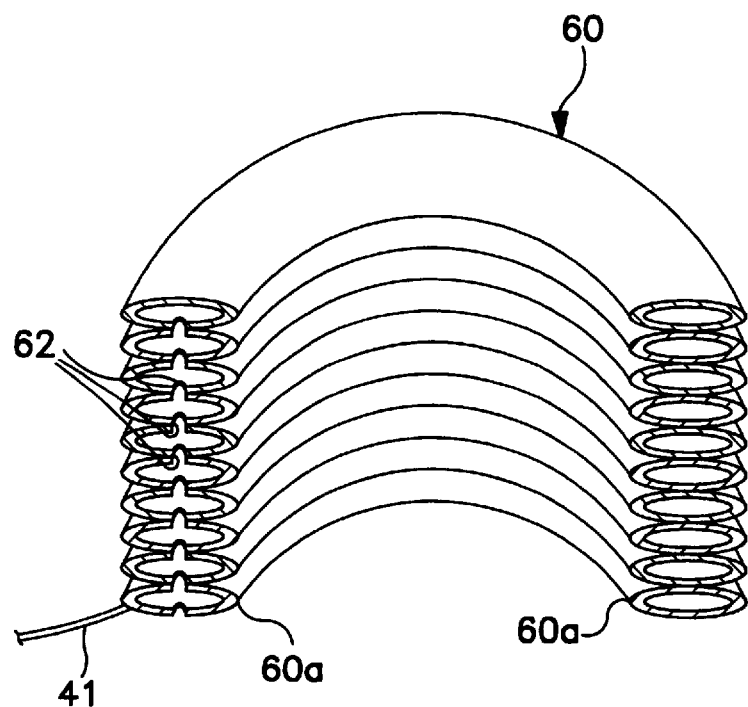
FIG. 3 is a perspective and fragmentary sectional view illustrating a plurality of tubes of the main feature of the traction apparatus according to the present invention.
Figure 4A:
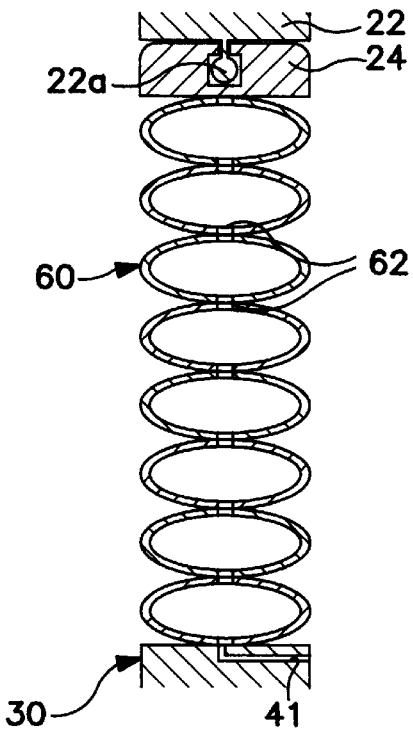
FIG. 4A and FIG. 4B are enlarged sectional views explaining the fluid supply and the fluid flow of the traction apparatus according to the present invention.
Figure 4B:
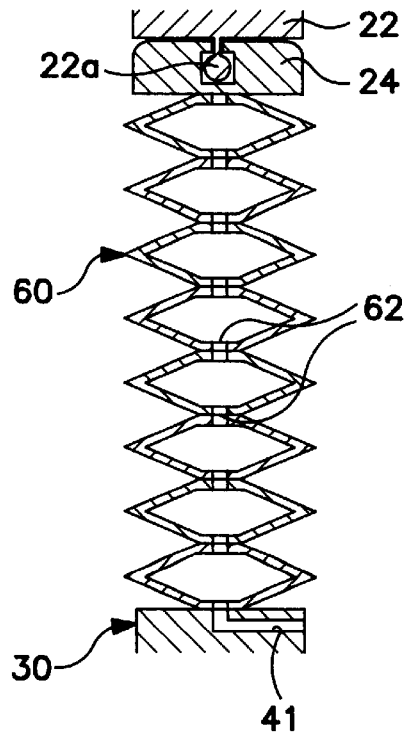
Figure 5:
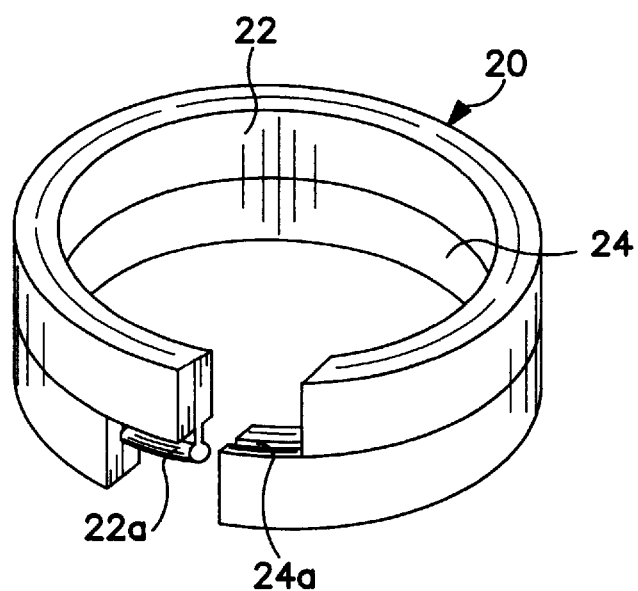
FIG. 5 is a perspective view of an exercising device of the traction apparatus according to the present invention.

Referring to FIG. 3, FIG. 4A and FIG. 4B, between the upper support frame 10 and the lower support frame 30, more accurately between the exercising device 20 and the lower support frame 30, a traction device 60 is disposed. The traction device is expandable to provide the traction on the therapy region in accordance with the operations of the automatic fluid generating device 45 or the manual fluid generating device 46. The traction device has a plurality of tubes which are integrally formed or are adhesively heaped together. Each of the tubes 60 forms a compartment with passage openings 62 at upper and lower sides thereof wherein the upper opening is in alignment with the lower opening to efficiently flow fluid. Each tube 60 have two free ends positioned in space relation therebetween and encircles the neck of human body with approximately circular shape. A lowermost tube 60a of the tubes 60 is sealably fitted with the aforementioned pipe 41 at a predetermined position to fill air up. FIG. 4A and FIG. 4B illustrate applicable sectional views of the tubes 60 with approximately elliptical shape and lozenge shape in cross section, respectively. And, since the tubes 60 are made of flexible plastic material, the patient wearing the traction apparatus can take flexion and extension exercises while undergoing traction. Again referring to FIG. 1, a plurality of ventilation holes 64 are formed between the tubes 60 as the openings 32 of the lower support frame 30.

Figure 2:
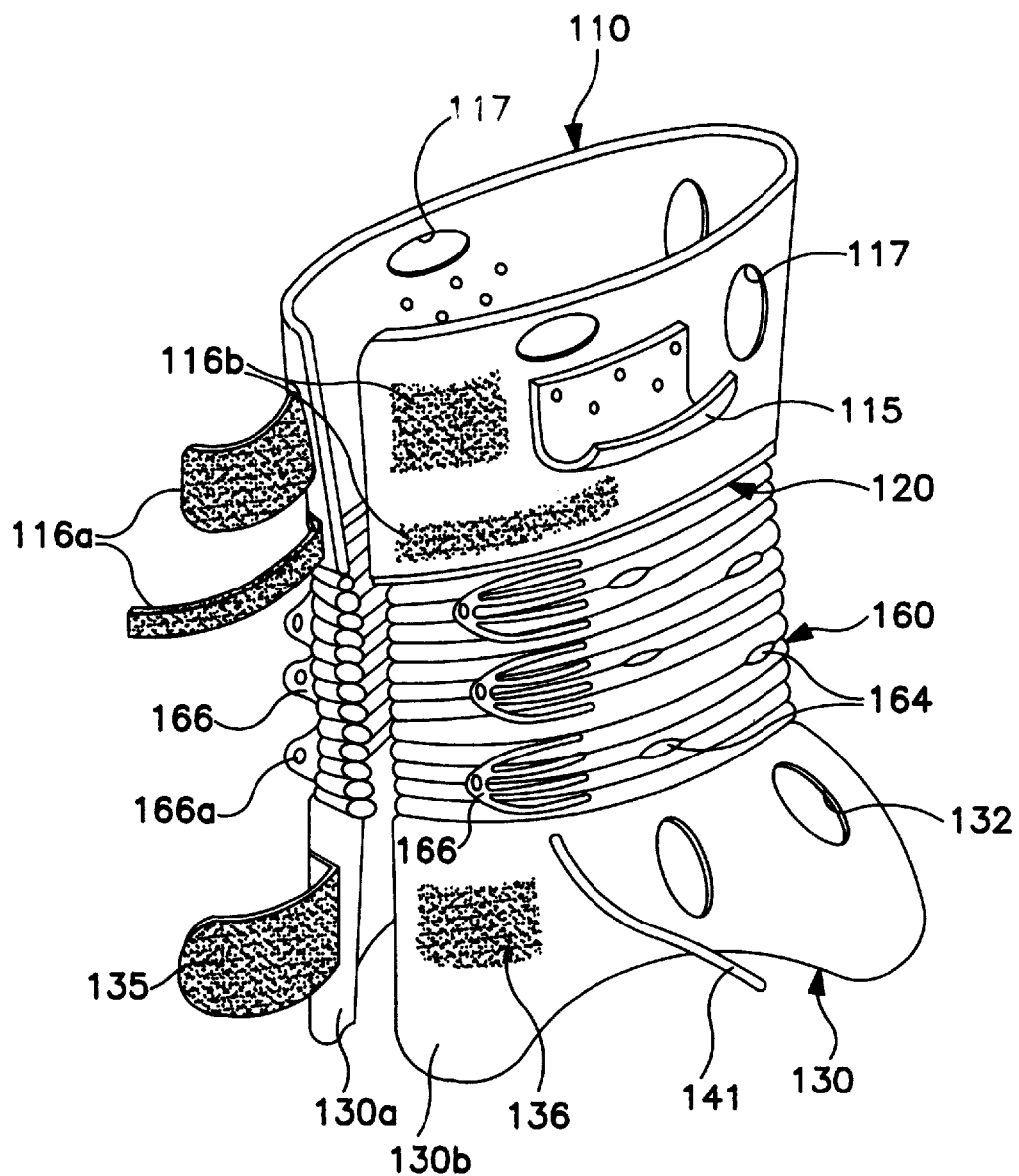
FIG. 2 is a perspective view of a traction apparatus according to the present invention which is used at the lumber region and shows the state of applying sufficient traction force.

Next, referring to FIG. 2, there is shown another embodiment of a traction apparatus for treating lumbar HNP according to the present invention, The traction apparatus for treating the lumbar HNP includes an upper support frame 110, a lower support frame 130 and a traction device 160 with a plurality of tubes as the aforedescribed traction apparatus for treating the cervical HNP. The upper support frame 110 encircles chest region and upper portion of the back of a human body and the lower support frame 130 encircles pelvis region. The upper support frame 110, the lower support frame 130 and the tubes 160 for the lumbar traction apparatus have the same substantial constitutions as the aforementioned cervical traction apparatus with some differences in shape and size. Now, the only differences between the lumbar and the cervical traction apparatus will be described. The differences depend on characteristics of the therapy region. Each armrest 115 is detachably provided at both left and right sides of the upper support frame 110 to prevent the upper frame 110 from moving upwardly. Ventilation openings 117 are formed at predetermined positions of the upper frame 110. The diameter of the tubes 160 is greater than that of the tubes 60 for the cervical region. Thus, since considerably voluminous quantity of flow is required to expand the tubes 160, several branched fixtures 166 are sticked to outer surfaces of the tubes 160 to prevent the tubes 160 from being twisted and bent. The fixtures 166 has a hole 166a at one end thereof to fasten the tubes 160 wherein a string (not shown) passes through the holes 166a to tie the tubes 160. On the other hand, in FIG. 2, unexplained numerals 116a, 116b, 135 and 136 designate VELCRO fasteners, numerals 130a and 130b designate end portions of the lower support frame 130, and numeral 141 designates a pipe 141. And, numerals 132 and 164 designate ventilation openings and holes, and numeral 120 designates a exercising device 120.

On the other hand, in the aforedescribed embodiments, preferably, the tubes 60 and 160 are made of flexible plastic material and specially the upper support frames 10, 110 and the lower support frames 30, 130 are made of foam plastic. Also, in FIG. 1, the upper and lower support frames 10, 30 and the tubes 60 has the two free ends at the back portions of the cervical traction apparatus, of course, the free ends may be formed at the front portions.

It is believed that the operation of the present invention may be easily understood from the aforedescribed constitutions of the embodiments without detailed explanations. Merely, the operation of the traction apparatus will now be briefly described to assist understanding of the present invention.

First, hot heat is applied to the therapy region by the electrotherapy device 50 to relax tonus of muscle and ligament. Then, the upper frames 10, 110 and the lower frames 30, 130 are suitably positioned on the therapy region of a patient. The end portions 12a, 13a and 130a, 130b of the frames 10, 30 and 110, 130 fasten together by means of VELCRO fasteners 16, 35, 36 and 116a, 116b, 135, 136 to connect the free ends of the frames 10, 30 and 110, 130. Second, the tubes 60, 160 are expandably filled up with air which is generated by the fluid generating devices 45 or 46 and is supplied through the pipe 41 and 141. Consequently, the expanded tubes 60, 160 provide traction on the therapy region to treat the corresponding HNP. On the other hand, the traction is determined by the air pressure and the quantity of air. The automatic fluid generating device 45 provides predetermined exact tractions and also cause the traction apparatus according to the present invention to perform pressure regulating function, timing function, intermittent ON and OFF function, etc. Finally, when the traction treatment is complete, the filled air in the tubes 60, 160 will be exhausted through the pipe 41, 141 by a known discharging device.

The invention is in no way limited to the embodiments described hereinabove. Various modifications of disclosed embodiments as well as other embodiments of the invention will become apparent to persons skilled in the art upon reference to the description of the invention. It is therefore contemplate that the appended claims will cover any such modification or embodiments as fall within the true scope of the invention.

What is claimed is:

1. A traction apparatus for physical therapy of a herniated nucleosus pulposus or sprain and strain comprising:

an upper support frame that supportably encircles an upper part of a patient's therapy region, said upper support frame having two free ends, having a space relation therebetween, with a first adjustable fastener that connects the two free ends;

a lower support frame that supportably encircles a lower part of the patient's therapy region, said lower support frame having two free ends, having a space relation therebetween, with a second fastener that connects the two free ends;

traction means operatively positioned between said upper support frame and said lower support frame for encircling the therapy region and for providing the therapy region with variable traction forces, said traction means having a plurality of expandable tubes stacked horizontally, wherein each of the tubes forms at least one closed compartment in flow communication with adjacent tubes and has two free ends having a space relation therebetween;

fluid pressure means for providing the traction forces; and exercise means, rotatable fixed between said upper support frame and an uppermost tube of the tubes, for exercising the patient's therapy region.

2. A traction apparatus as claimed in claim 1, wherein each of the tubes has passage openings on upper and lower portions thereof and wherein the opening on the upper portion is in alignment with the opening on the lower portion to allow efficient flow fluid.

3. A traction apparatus as claimed in claim 1, wherein said exercising means comprises a first cooperation member with a groove formed along a center line of top surface thereof, the first member being fixed to the uppermost tube; and a second cooperating member with a protrusion formed along a center line of bottom surface thereof and slidably fitted with the groove of the first cooperation member, the second member being fixed to said support frame.

4. A traction apparatus as claimed in claim 1, wherein said traction means has a plurality of ventilating holes between the tubes to have good ventilation at the patient's therapy region.

5. A traction apparatus as claimed in claim 1, wherein the first and second fasteners are hook and loop fasteners.

6. A traction apparatus as claimed in claim 1, wherein said supplying means comprises a pipe connected to one of the tubes through said lower support frame, and a fluid pressure generating device operatively provided at one end of the tube to supply the fluid pressures and to remove the supplied fluid pressures.

7. A traction apparatus as claimed in claim 1, wherein said upper support frame has two armrests at both sides thereof to support arms and to prevent said upper support frame from moving upwardly.

* * * * *